United States Patent [19]
Johnson et al.

[11] Patent Number: 5,766,839
[45] Date of Patent: Jun. 16, 1998

[54] PROCESSES FOR PREPARING BARRIER LAYER FILMS FOR USE IN ENZYME ELECTRODES AND FILMS MADE THEREBY

[75] Inventors: Jay M. Johnson, Dayton; Jeffrey L. Huntington, Yellow Springs, both of Ohio

[73] Assignee: YSI Incorporated, Yellow Springs, Ohio

[21] Appl. No.: 618,529

[22] Filed: Mar. 19, 1996

Related U.S. Application Data

[63] Continuation-in-part of Ser. No. 261,445, Jun. 17, 1994, abandoned.

[51] Int. Cl.$^6$ .............................. C12Q 1/00; G01N 27/26
[52] U.S. Cl. ................. 435/4; 204/400; 204/415
[58] Field of Search .......................... 435/4; 204/400, 204/415

[56] References Cited

U.S. PATENT DOCUMENTS

| | | | |
|---|---|---|---|
| 3,979,274 | 9/1976 | Newman | 204/195 B |
| 4,073,713 | 2/1978 | Newman | 204/195 B |
| 4,241,178 | 12/1980 | Esders et al. | 435/15 |
| 4,388,166 | 6/1983 | Suzuki et al. | 204/403 |
| 4,415,666 | 11/1983 | D'Orazio et al. | 435/179 |
| 4,418,148 | 11/1983 | Oberhardt | 435/179 |
| 4,467,811 | 8/1984 | Clark, Jr. | 128/635 |
| 4,484,987 | 11/1984 | Gough | 204/1 T |
| 4,759,828 | 7/1988 | Young et al. | 204/1 T |
| 4,786,597 | 11/1988 | Matson et al. | 435/41 |
| 4,795,707 | 1/1989 | Niiyama et al. | 435/288 |
| 4,832,797 | 5/1989 | Vadgama et al. | 204/1 T |
| 4,855,353 | 8/1989 | Kurami et al. | 525/54.1 |
| 4,886,740 | 12/1989 | Vadgama | 435/4 |
| 4,950,379 | 8/1990 | Young et al. | 204/403 |
| 5,352,348 | 10/1994 | Young et al. | 204/153.12 |
| 5,429,726 | 7/1995 | Johnson et al. | 204/153.12 |

FOREIGN PATENT DOCUMENTS

| | | |
|---|---|---|
| 1307826 | 9/1992 | Canada . |
| 0216577 | 4/1987 | European Pat. Off. . |
| 54-43796 | 4/1979 | Japan . |
| 55-162051 | 12/1980 | Japan . |
| 59-164953 | 9/1984 | Japan . |
| 60-185153 | 9/1985 | Japan . |
| 61-145447 | 3/1986 | Japan . |
| 1442303 | 7/1976 | United Kingdom . |
| 9204438 | 3/1992 | WIPO . |

OTHER PUBLICATIONS

Johnston, et al. : Effect of secondary additives in casting . . . : J. App. Pol. Sci. 17: pp. 2485–2499, 1973.
Teijin: Ultrafiltration membranes: CA 99:106450, 1983.
Teijin: Cellulose membranes: CA 99:72428, 1983.
Teijin: Semipermeable membranes: CA 98:5241, 1981.
Hawley's Condensed Chemical Dictionary, Twelfth Ed., Rev. by Richard J. Lewis, Sr.:Van Norstrand Reinhold Company, NY, 1981.
He: Research on CA–CAB mixed membranes for reverse osmosis: Second Inst. Oceanogr., SOA, Hangzhou, P.R.O.C.: abstract, 1991.
Bodmeier, et al.: Hydrolisis of cellulose acetate . . . : Drug Dev. and Ind. Pharm. : 19 (5): pp. 521–530, 1993.
Kutowy, et al. : Cellulose acetate ultrafiltration membranes: J. App. Pol. Sci. : 19: pp. 1449–1460, 1975.
Article: "The Effect Of Crosslink Density On Permeability In Biosensors: An Unsteady–State Approach" Biotechnology Techniques, vol. 9 No. 4, 1995 pp. 277–282 by Mehmet Mutlu and Selma Mutlu.
Article: "Generalized model for enzyme amperometric biosensors" Analytica Chimica ACTA 307 (1995), pp. 27–36 by Alexander Neikov and Sokol Sokolov.
Article: "A Model for the Amperometric Enzyme Electrode Obtained through Digital Simulation and Applied to the Immobilized Glucose Oxidase System" 1974 by Leroy D. Mell and J.T. Maloy.
Article: "The Size of Pores In Collodion Membranes" by David I. Hitchcock, Laboratories of The Rockefeller Institute for Medical Research, accepted for publication Mar. 1, 1926.
Article: "Statistical Evaluation Of Sieve Constants In Ultrafiltration" Laboratories of the Hopkins Marine Station, Pacific Grove, accepted for publication Nov. 30, 1935 by John D. Perry.
Article: "Passage of Molecules Through Capillary Walls" by John R. Pappenheimer, Department of Physiology, Harvard Medical School.
Article: "Filtration, Diffusion and Molecular Sieving Through Peripheral Capillary Membranes—A Contribution to the Pore Theory of Capillary Permeability" by J.R. Pappenheimer, E.M. Renkin and L.M. Borrero, Department of Physiology, Harvard Medical School, Boston MA.
Hawley's Condensed Chemical Dictionary, Twelfth Edition, Revised by Richard J. Lewis, Sr (1981) Van Nostrand Reinhold Company, NY.
Review: Transport Phenomena In Membranes, N. Lakshminarayanaiah, Academic Press, New York, 1969, submitted by Herbert P. Silverman, Ph.D.

(List continued on next page.)

*Primary Examiner*—Ponnathapura Achutamurthy
*Assistant Examiner*—Brett L. Nelson
*Attorney, Agent, or Firm*—Biebel & French

[57] ABSTRACT

Methods for forming thin layer barrier layer films for use in enzyme containing laminated membranes and membranes formed thereby are disclosed. The barrier layers exhibit improved acetaminophen rejection and comprise a cellulose acetate/cellulose acetate butyrate blend. The thin layer barrier membranes are formed from a plural solvent containing solution and are cured at a critical temperature of about 102°–114° F., most preferably at about 106° F.–114° F. while traveling through a circulating hot air oven. Alternatively, the membranes can be cured at room temperature or in a stagnant oven at temperatures of from room temperature to about 175° C. (350° F.) for a period of from about 10 minutes to 1 hour.

50 Claims, 5 Drawing Sheets

OTHER PUBLICATIONS

Nuclepore Filtration Products for the Laboratory, Catalog LAB 30.

"Hydrolysis of Cellulose Acetate and Cellulose Acetate Butyrate Pseudolatexes Prepared by a Solvent Evaporation–Microfluidization Methed" Drug Development and Industrial Pharmacy, 19(5), 521–530 (1993) by Roland Bodmeier et al.

Article: "Elimination of the Acetaminophen Interference in an Implantable Glucose Sensor", Analytical Chemisty, vol. 66, No. 7, pp. 1183–1188 (1994) by Yanan Zhang et al.

Article: "Cellulose Acetate Ultrafiltration Membranes" Journal of Applied Polymer Science, vol. 19, pp. 1449–1460 (1975) by O. Kutowy et al.

Article: "Effect of Secondary Additives in Casting Solution on the Performance of Porous Cellulose Acetate Reverse Osmosis Membranes" Journal of Applied Polymer Science, vol. 17, pp. 2485–2499 (1973) by H. Kirk Johnston et al.

Article: "Effect of Casting Conditions on the Performance of Porous Cellulose Acetate Membranes in Reverse Osmosis" Journal of Applied Polymer Science, vol. 14, pp. 723–733 (1970) by B. Kunst et al.

"Paracetamol Interference with Glucose Analysis" The Lancet, Sep. 19, 1981.

"Paracetomol Interference with Glucose Analyser" Clinical Chemisty, vol. 27, No. 11 (1981).

"Electrochemical Interferences with the YSI Glucose Analyzer" Clinical Chemistry, vol. 28, p. 726 (1982).

"Paracetamol and Blood–Glucose Analysis with the YSI Analyzer" Clinical Chemistry, vol. 29, No. 12 (1983).

"Acetaminophen Overdose—A new–and treacherous–care problem" Registered Nurse Magazine, Dec. 1978 pp. 56–62 by John S. Jozwiak, R.N., B.S.N.

"Paracetamol Interference with YSI Glucose Analyzer" Clinical Chemistry, vol. 27, No. 5, pp. 782–783 (1981).

"Apparent hyperglycaemia in paracetamol overdose" British Journal of General Practice, Jun. 1992.

"Evaluation of the YSI 2300 Glucose Analyzer: Algorithm–corrected Results are Accurate and Specific", Clinical Biochemistry, vol. 29 (1996) by J. Rex Astles et al.

"Reverse Osmosis Membranes" Journal of Applied Polymer Science, 15, 1317, 1319.

"Internal membranes and laminates for adaptation of amperometric enzyme electrodes to direct biofluid analysis" Scand J. Clin Lab Invest 1993; 53, Suppl 214: 53–60 by Mohamed A. Desai et al.

"Amperometric enzyme electrodes for lactate and glucose determinations in highly diluted and undiluted media" Analytica Chimica Acta, 281 (1993) 489–502 by Dorothea Pfeiffer et al.

"Plasticized poly(vinyl chloride) as a permselective barrier membrane for high–selectivity amperometric sensors and biosensors" Analytica Chimica Acta, 269 (1992) 65–73 by I.M. Christie et al.

Journal of Applied Polymer Science, p. 1878 by R.E. Kesting et al.

Article: "Diffusion of Protein Molecules Through Membranes of Controlled Pore Size" Biochemical and Biophysical Research Communications, vol. 5, No. 3, (1961), pp. 196–202 by Eckhardt Fuchs and George Gorin.

Article: "Dialysis Studies III. Modification of Pore Size and Shape In Cellophane Membranes" by L.C. Craig and Wm. Konigsberg Rockefeller Institute Laboratories, New York, NY Aug. 5, 1990 pp. 166–172.

Article: "Characterization Of Biological Membranes by Equivalent Pores" by A.K. Solomon, Biophysical Laboratory, Harvard Medical School, Boston, MA, pp. 335–364.

Article: "Preparation And Characterization Of Polymeric Membranes Of Graded Porosity" by Harry P. Gregor and Edward Kantner, Mar. 14, 1967, pp. 1169–1171.

Article: "On The Permeation Of Cellophane Membranes By Diffusion" by L.B. Ticknor, Apr. 21, 1958–pp. 1483–1485.

Article: "Dialysis Studies. VI. Experiments With Amino Acids" by Lyman C. Craig and Allen Ansevin, Laboratories of Rockefeller Institute, New York City, May 20, 1963, pp. 1268–1271.

Article: "Restricted Diffusion Of Macromolecules Through Agar–Gel Membranes" by G.K. Ackers and R.L Steere, Plant Virology Laboratory, Crops Research Div., Agricultural Research Service, Bellsville, MD, Sep. 26, 1961, pp. 137–148.

Article: "Membrane Diffusion Studies With Proteins And Nuleic Acids" Jack Goldstein and Lyman C. Craig, The Rockefeller Institute, New York, NY, Feb. 17, 1960, pp. 1833–1834.

Article: "Fractional Dialysis With Cellophane Membranes" Laboratories of the Rockefeller Institute for Medical Research, New York, NY, Jul. 5, 1956, by Lyman C. Craig et al., pp. 4171–4172.

Article: "Some Dialysis Eoxeriments With Polypeptides" by L.C. Craig et al., Jul. 11, 1955, Rockefeller Institute For Medical Research, New York, NY, pp. 6620–6624.

Article: "Dialysis Studies. II. Some Experiments Dealing With The Problem Of Selectivity" by Lyman C. Craig et al., Laboratories Of The Rockefeller Institute For Medical Research, Feb. 6, 1967, pp. 3729–3737.

Article: "A Physical Interpretation Of The Phenomenological Coefficients Of Membrane Permeability" The Journal Of General Physiology, vol. 45, (1961) by O. Kedem et al, Weizmann Institute Of Science, Rehovoth, Isreal, pp. 143–179.

Article: "Ultrafilter Membranes And Ultrafiltration" by John Douglass Ferry, Department of Chemistry, Stanford University, California, Oct. 28, 1935, pp. 373–455, Chemical Reviews, vol. 18, No. 3.

Teisin, "UltraFiltration Membranes", CA 99:106450 (1983).

Teisin, "Cellulose Membranes", CA 99:72428 (1983).

Teisin, "Semipermeable Membranes", CA 98:5241 (1981).

He, "CA–LAB Mixed Membranes", CA 116:241635 (1991).

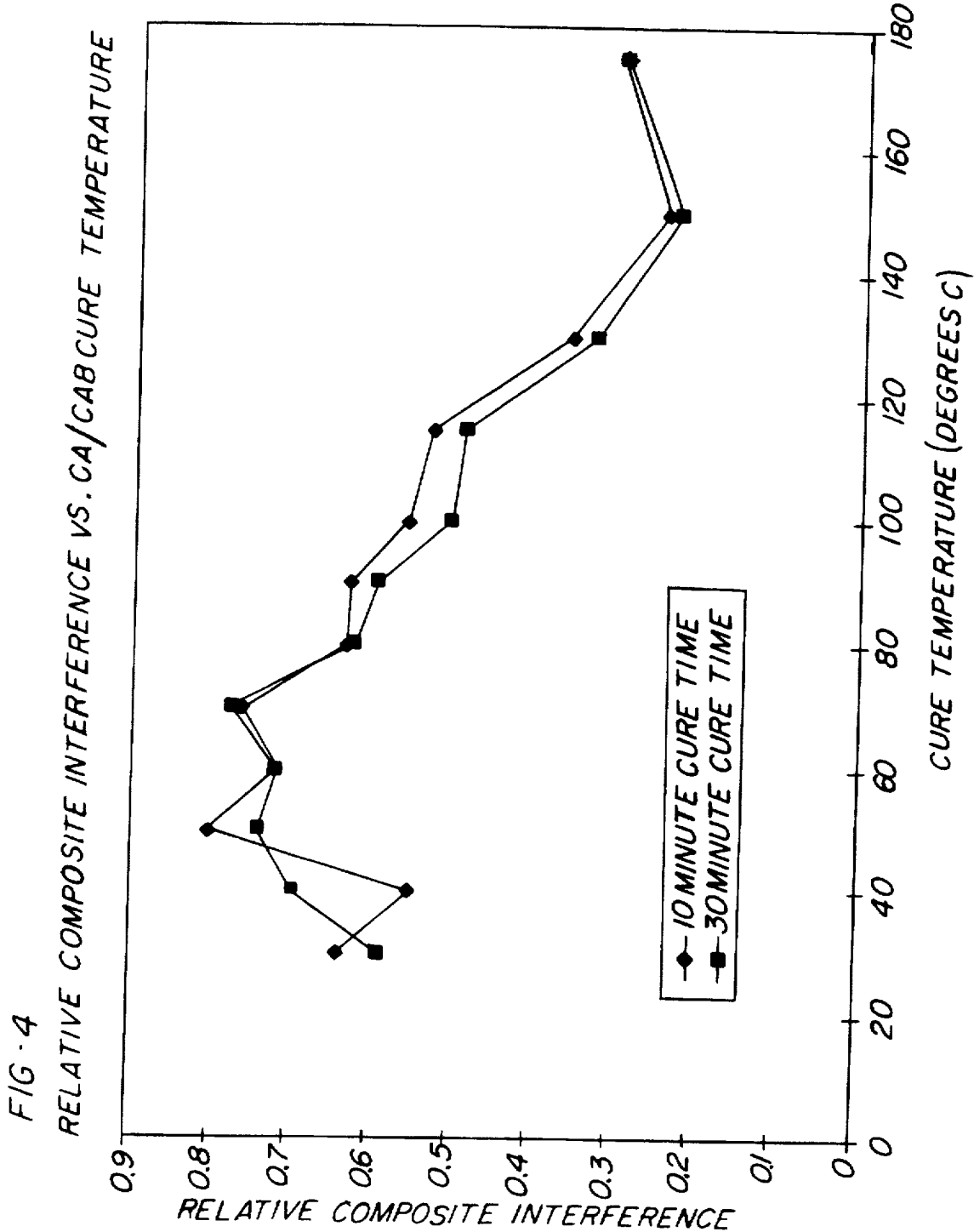

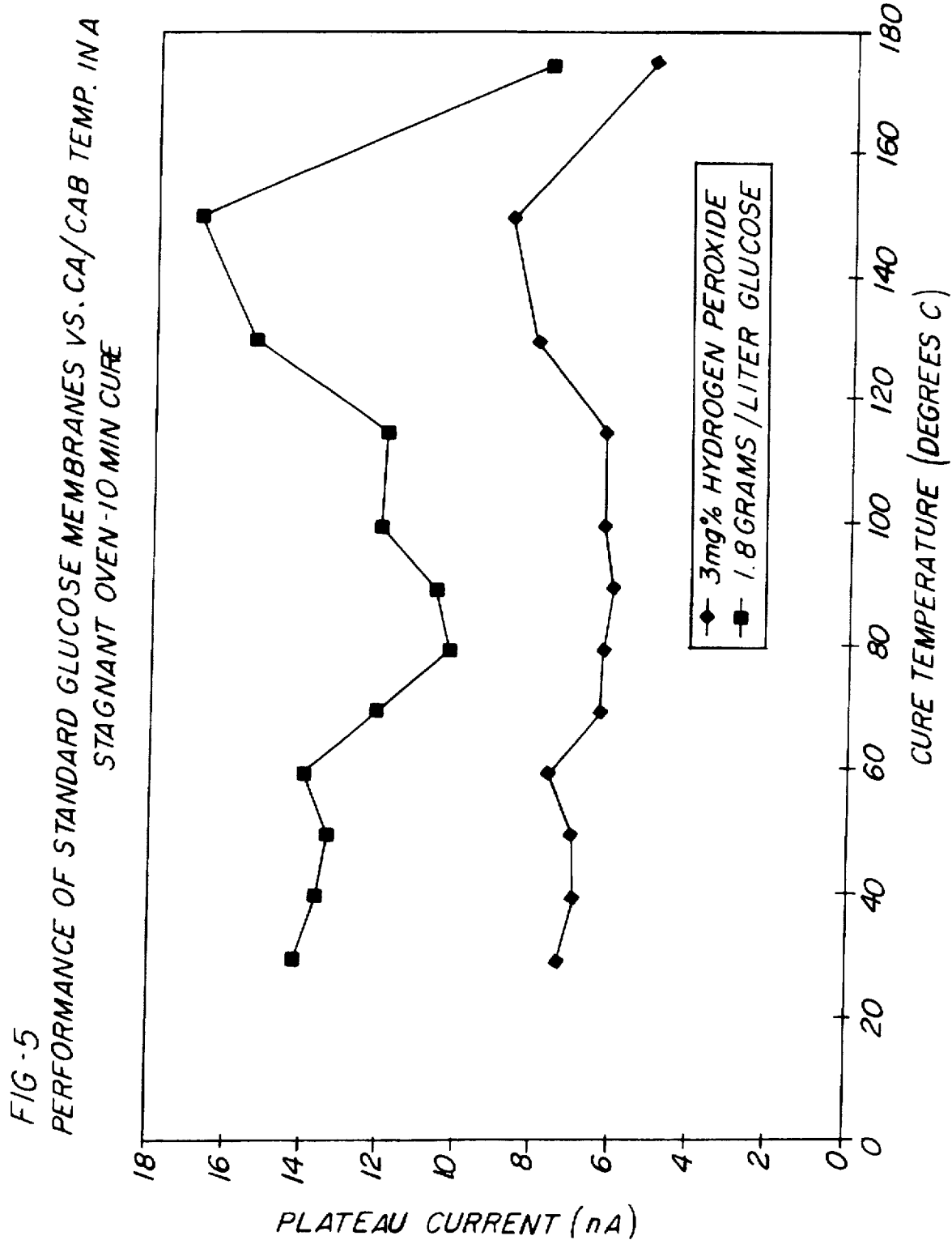
FIG-5 PERFORMANCE OF STANDARD GLUCOSE MEMBRANES VS. CA/CAB TEMP. IN A STAGNANT OVEN-10 MIN CURE

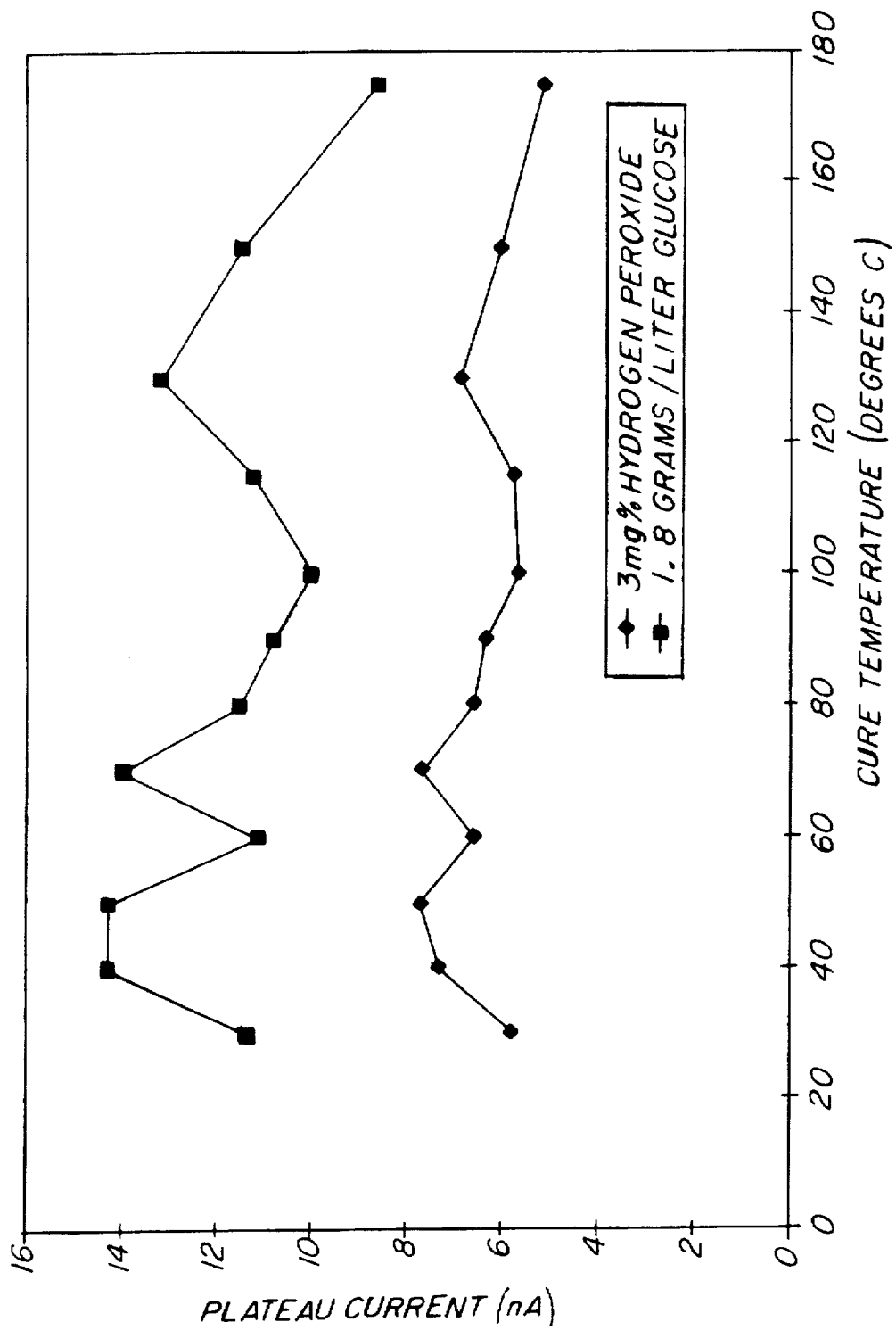
FIG-6 PERFORMANCE OF STANDARD GLUCOSE MEMBRANES VS. CA/CAB CURE TEMP. IN A STAGNANT OVEN 30 MIN CURE

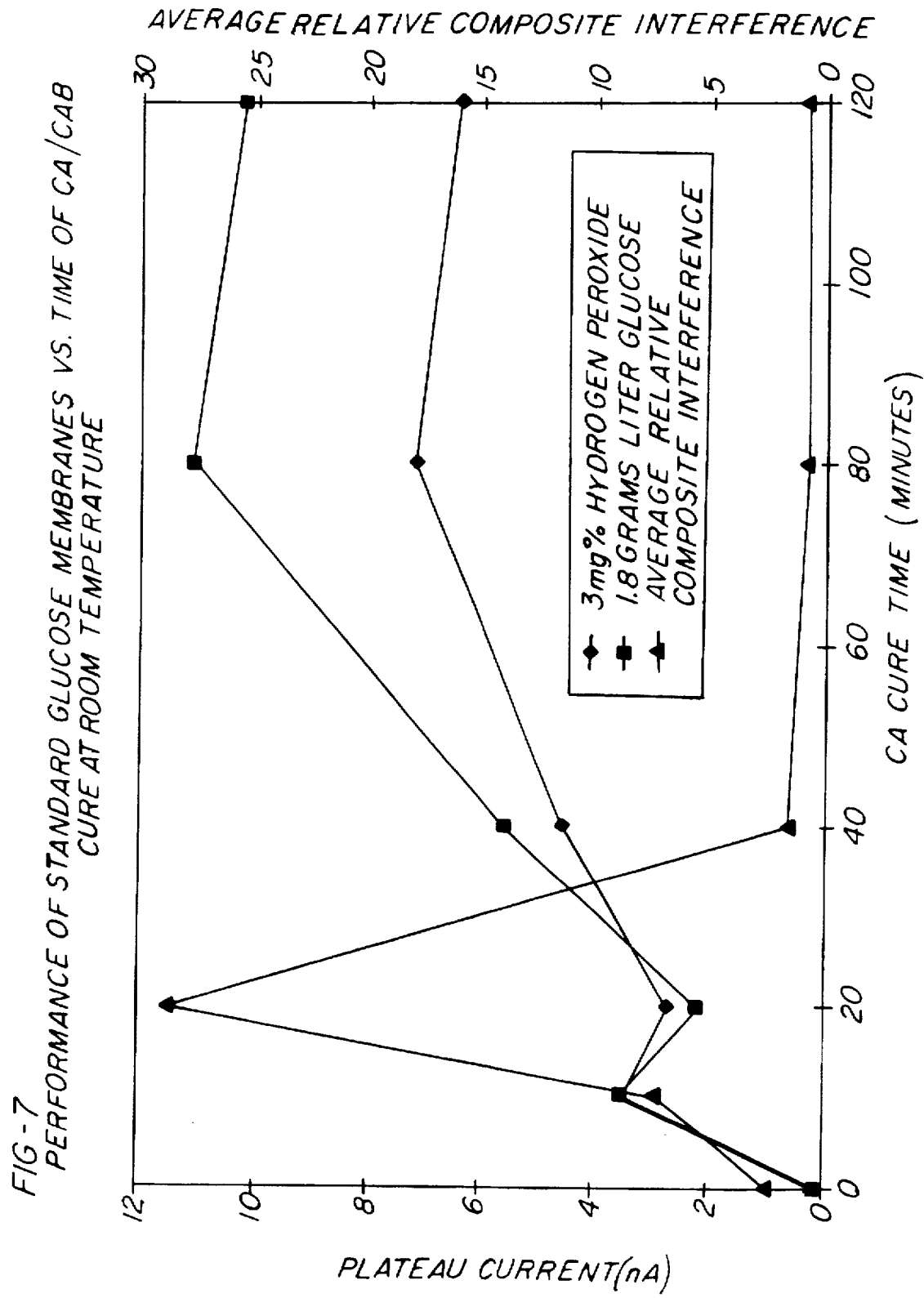

PROCESSES FOR PREPARING BARRIER LAYER FILMS FOR USE IN ENZYME ELECTRODES AND FILMS MADE THEREBY

CROSS REFERENCE TO RELATED APPLICATIONS

The present application is a continuation in part of application Ser. No. 08/261,445 filed Jun. 17, 1994 now abandoned.

FIELD OF THE INVENTION

The invention pertains to improved methods for forming this barrier layer films that are useful as a component of an enzyme containing laminated membrane.

BACKGROUND OF THE INVENTION

Polarographic cell systems have met with wide acclaim particularly in the medical field, providing for detection and concentration measurement of many desired analytes. Enzymes are commonly used in such systems, especially in those situations wherein the analyte itself is not polarographically active but where a reaction product formed or reactant consumed by an enzymatic reaction with the analyte is polarographically active.

For example, in medical applications, one common procedure is to measure glucose in the blood of a patient. Typically, blood samples are withdrawn from the patient for an in-line analysis for glucose concentration using a glucose oxidase electrode with a polarographic detector for detecting $H_2O_2$ generated in accordance with the reaction:

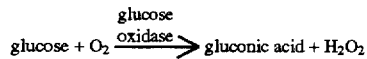

The hydrogen peroxide generated by the reaction is measurable by a polarographic detector and, by appropriate calibration and calculation, glucose content in the sample can be accurately determined by the $H_2O_2$ formed in the reaction.

The polarographic cell systems commonly used for these measurements include an enzyme containing laminated membrane that separates the analyte sample from the working electrode of the cell. These types of membranes are disclosed in U.S. Pat. Nos. 3,979,274 and 4,073,713 (Newman), both patents being hereby incorporated by reference herein. In such membranes, a thin innermost membrane referred to as a barrier layer composed of cellulose acetate, silicone rubber, or methyl methacrylate is located adjacent the working electrode of the polarographic cell. Glucose oxidase enzyme is interposed between this barrier layer and an outer polycarbonate support layer. The outer support layer is typically about 5 μm in thickness and is in contact with the analyte containing sample.

In a glucose analytical determination, glucose and oxygen permeate through the outer support layer and react in the presence of the enzyme. Hydrogen peroxide produced permeates through the inner barrier layer where it is polarographically detected. The support layer permits passage of glucose, oxygen and other molecules therethrough while not permitting passage of high molecular weight substances such as proteins, red blood cells and other macromolecules.

The barrier layer permits access of hydrogen peroxide to the working electrode while blocking passage of substances having molecular weights on the order of about 250 and greater such as ascorbic acid and uric acid.

One problem that has been encountered in polarographic systems as described above is that acetaminophen [N-(4-hydroxy phenyl) acetamide] in the blood sample analyzed is itself polarographically detectable. This causes inaccurate readings when attempts are made to monitor glucose levels in whole or diluted blood samples.

The problem of acetaminophen interference in glucose determination is especially grave because plasma glucose level is one of the factors used to assess the severity of acetaminophen poisoning. In a case of suspected acetaminophen poisoning, an episode of low plasma glucose is diagnostic of massive liver damage and indicates that heroic measures will be needed to save the life of the patient. However, a glucose membrane susceptible to acetaminophen interference will give an apparently elevated glucose reading, even when the actual plasma glucose is low, completely obscuring the diagnosis.

Accordingly, there is a need in the art to provide a method for making improved films that are to be incorporated as the barrier layer in an enzyme containing laminated membrane.

Practical considerations dictate that the barrier layer construction will inhibit acetaminophen migration therethrough while not substantially impeding migration of $H_2O_2$ to the working electrode. In polarographic systems of the type described supra, it is desirable to permit as much of the $H_2O_2$, produced via the enzymatic reaction, to reach the electrode to thereby result in an easily detectable current. Barrier membranes that inhibit acetaminophen migration at the expense of instrument sensitivity are of no significant advantage.

It is therefore an object of the invention to provide a method for producing a barrier layer that will effectively inhibit acetaminophen migration to the working electrode while maintaining a desired instrument sensitivity level.

Additionally, hydroxyurea, potassium iodide, and isoniazid are also therapeutically used agents that may be contained in blood samples. These also result in false glucose readings similar to those provided upon acetaminophen presence in the blood. Accordingly, it is an additional object of the invention to provide a barrier membrane that will also inhibit hydroxyurea, potassium iodide, and isoniazid migration to the electrode while permitting the desired electrically detectable species, for example, $H_2O_2$ to pass therethrough substantially unimpeded to thereby result in an acceptable electrical sensitivity.

PRIOR ART

Cellulose acetate, silicone rubber or methyl methacrylate barrier film layers for incorporation into an enzyme containing laminated membrane are taught in the aforementioned Newman patents. Preferred barrier films taught in this patent are homogenous films composed of cellulose acetate made by a "water casting" technique. In accordance with this technique, the cellulose acetate is dissolved in cyclohexanone and the resulting solution is dropped into a quiescent pool of water. The cellulose acetate precipitates on the top of the water and is removed therefrom by a strippable carrier sheet such as polyethylene. Suitable cellulose acetate films having thicknesses less than 2 microns may be produced by this method.

Canadian patent 1,307,826 discloses barrier membranes that may be composed of silicone rubber, methyl methacrylate or other porous and permeable material such as cellulose acetate butyrate or cellulose acetate. Preferably, the barrier layer comprises cellulose acetate. As reported in this patent, these inner membranes have thicknesses of from 2–10 mu and are prepared from an acetone/cyclohexanone solution spread onto the surface of a glass plate using a microfilm applicator.

It is difficult or impossible to remove films from a glass plate if the film is cured entirely by air drying. Extracting the solvent(s) from the film by flooding with water permits removal of the film from the backing but also produces an asymmetric film with mainly coarse pores. The intrusion of water into the film results in a phase inversion process in which the film is solidified in the form of a gel thereby resulting in a heterogenous structure exhibiting inconsistent pore shape and non-uniform pore distribution throughout.

Most combinations of resins and solvents cannot be water cast at all. Even those that can are erratic and unpredictable in the way they spread over the surface of the water. Since the film thickness and pore geometry depend very strongly on the way the casting dope spreads over the surface of the water, reproducible results cannot be expected. In particular, solutions in solvent other than cyclohexanone spread very poorly over the water.

Thick CA/CAB films cured by drying with hot air give slow responses and low sensitivities to glucose. Their permeability to hydrogen peroxide is too low.

Some acetaminophen interference problems were experienced in conjunction with the YSI Model 23A analyzer. In order to help overcome these problems, thick cellulose acetate/cellulose acetate butyrate (CA/CAB) membranes having average thicknesses of about 6 microns were used in laminated enzyme membrane structures of the type disclosed in the Newman patents. These thick CA/CAB membranes were made by a knife blade casting technique in which a doctor's blade was appropriately spaced over the casting solution which was in turn superimposed over the desired polymeric substrate. The casting solution was similar to that used in the instant invention (i.e. the CA/CAB polymers were cast in a solution comprising nitromethane and γ-butyrolactone). Films cast from this solution were cured by baking at high temperature of about 150° C. (300° F.).

These films, when incorporated as barrier layers in Newman-type membranes, served to provide satisfactory protection against false readings caused by acetaminophen presence, but they resulted in slow instrument response time. However, performance of these membranes on the Model 23A machines was acceptable.

The shift toward quicker, fully automated systems, led to the introduction of the YSI Model 2300 series analyzers in 1989. These analyzers place much more emphasis on rapid measurement and include fully automatic, programmable measurement time intervals and measurement cell flush out timing cycles. The aforementioned thick, CA/CAB membranes proved unacceptable for use in conjunction with the 2300 series analyzers because they took too long to obtain plateau currents (i.e., measurement time was too long) and adequate membrane flushing could not be accomplished within the flushing time periods allotted by the machine for the sample measurement.

Due to the poor performance of the thick CA/CAB membranes in the 2300 series analyzers, the thin water cast CA films disclosed in the Newman patents were then used as the barrier layer component of the laminated membrane assembly in the 2300 systems. Although these barrier layers provided for adequate measurement time and could be adequately flushed within the allotted time period, they did not serve to reduce acetaminophen interference.

It was not until the presently claimed methods and barrier layer films made thereby were discovered that an acetaminophen rejecting barrier layer could be successfully employed in a laminated membrane structure for our 2300 series analyzers. Use of the CA/CAB barrier layers in accordance with the invention not only are effective in inhibiting acetaminophen interference but they also significantly provide rapid measurement time and they can be adequately flushed within the instrument's flushing cycle requirements.

Accordingly, despite the prior art efforts, there remains a need for a method to produce thin barrier films on the order of 2 μm and less, which films function to inhibit false polarographic detector readings caused by acetaminophen in the sample, without significantly decreasing instrument sensitivity. There is an additional need to provide methods for forming barrier films that will also serve to inhibit hydroxyurea, potassium chloride, and isoniazid interference.

SUMMARY OF THE INVENTION

These and other objects are met by the present methods and barrier films made thereby.

The barrier film is a thin (i.e. 2 micron or less) cellulose acetate(CA)/cellulose acetate butyrate (CAB) film which is solvent cast from a plural component non-aqueous solvent system. The film may be produced using a conventional Mayer-rod coating machine. Curing temperatures of the casting solution are carefully controlled.

At least two solvents are employed to dissolve the CA/CAB blend. A volatile solvent such as nitromethane, dimethylformamide, cyclohexanone, etc is used in combination with a liquid plasticizer. A casting solution containing CA, CAB, and the solvents is spread over a suitable carrier sheet to the desired thickness via conventional mayer-rod coating techniques using for example machinery purchased from Lamitec, Inc., Minneapolis, Minn.

After the CA/CAB solution is applied to the carrier sheet in the desired thickness (i.e. a sufficient amount to result, after curing, in a 2 micron or less film) it is then forwarded to an oven for curing. Temperature of the curing step in the oven is strictly controlled to a range of about 102° F. to 114° F. The cured film resides in the oven for about 0.5 to 1.5 or from about 0.5–10 minutes. The film is advanced to a take-up roll.

In another embodiment of the invention, the desired non-aqueous solvent system including the CA/CAB is spread over a desired substrate such as PET in a thickness that will ultimately result in a cured film thickness of about 2 microns or less. The precursor solvent containing solution is then cured at a temperature of room temperature to about 350° F. or less.

The invention will be further described in conjunction with the attached drawings and following detailed description.

BRIEF DESCRIPTION OF THE DRAWINGS

FIG. 4 is a graphical representation showing relative interference inhibition efficacy versus barrier layer curing temperatures in accordance with an alternative process for making the barrier layer;

FIG. 5 is a graphical representation showing electrical sensitivity versus barrier layer curing temperatures in accordance with the alternative process;

FIG. 6 is a graphical representation similar to that shown in FIG. 5. but relating to data collected for a longer curing time than the data presented in FIG. 5; and FIG. 7 is a graph showing the electrical sensitivity and interference efficacy of the alternative process room temperature barrier film curing compared to room temperature curing times.

DETAILED DESCRIPTION OF THE EMBODIMENT

Figure 1:
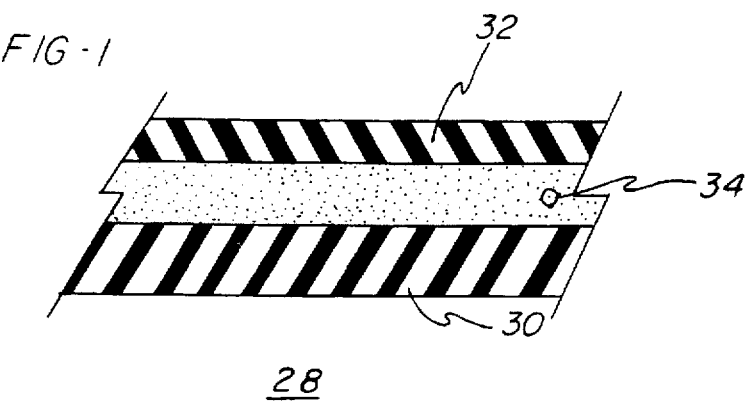
FIG. 1 is an enlarged view of a cross-section of an enzyme containing laminated membrane.

With reference made to FIG. 1 of the drawings, there is shown an enlarged cross-section of an enzyme containing laminated membrane 28. Membrane 28 is adapted for use in conjunction with commercially available analytical equipment such as the Models 1500, 2700 or 2300 stat analyzers available from The Yellow Springs Instrument Co., Inc. Yellow Springs, Ohio.

Barrier layer 32 comprises an homogenous cellulose acetate/cellulose acetate butyrate polymer blend having a thickness of 2 microns or less, preferably 1–2 microns. Enzyme 34 is provided intermediate barrier layer 32 and support layer 30. Enzyme 34 is typically cross-linked in situ between the layers 32,30 by use of glutaraldehyde although any one of a number of adhesives or cross-linking promoters may be used. Also, it should be mentioned that the enzyme itself may be used as the adhesive without any additional adhesive or cross-linking agent added.

Support layer 30, as shown, is composed of a polycarbonate layer such as those that are commercially available from Nuclepore Filtration Products of Pleasanton, Calif. under the "Nucleopore" brand name. Other acceptable films may be purchased from Poretics, Inc. of Livermore, Calif. These films typically have thicknesses ranging from about 5 to 7 microns.

As shown, support layer 30 comprises a single layer. It is to be understood however, that the support layer 30 may actually comprise a multi-layered structure with, for example, bovine serum albumin or other suitable adhesive interposed between layers to yield a composite structure. In this approach pore sizes and individual thicknesses of the layers can be controlled, for instance, to limit or promote migration of a given chemical species to the enzyme 34.

It is to be appreciated that support layer 30 is positioned adjacent the analyte sample and that the barrier layer 32 is therefore adjacent a working electrode (typically platinum) in an electrolyte solution. An auxiliary electrode is also disposed in the electrolyte. Accordingly, a polarographic cell is provided in which the electrodes and electrolyte are separated from the analyte solution by the laminated membrane.

As used throughout this disclosure, enzyme 34 will be described as glucose oxidase enzyme. The artisan of course will appreciate that depending on the particular desired analyte and reaction chosen, the enzyme may vary. For instance in analytical situations in which it is desired to monitor lactate levels in blood samples, lactate oxidase will be used as enzyme 34. Other candidate analytes and corresponding oxidoreductase enzymes are noted as being exemplary:

| analyte | oxidoreductase enzyme |
|---|---|
| lactose | galactose oxidase |
|  | ( invertase |
| sucrose | ( mutarotase |
|  | ( glucose oxidase |
| alcohol | alcohol oxidase |
| galactose | galactose oxidase |

Membrane 32 is composed of a blend of cellulose acetate/cellulose acetate butyrate cellulosic esters. The ratio (by weight) of cellulose acetate: cellulose acetate butyrate used to form barrier layer 32 varies widely over a range of 1.5–20:1. Based upon present indications, it is preferred to utilize a 4:1 (by weight) blend of cellulose acetate/cellulose acetate butyrate to cast the film used to form barrier layer 32 of membrane 28.

The requisite ratio of cellulose acetate and cellulose acetate butyrate is dissolved in a two solvent non-aqueous system. The first solvent is a highly volatile organic solvent exhibiting a low boiling point. At present, nitromethane, dimethylformamide and cylcohexanone may be mentioned as being exemplary members of this class of highly volatile organic solvents. All of those have boiling points, under atmospheric conditions, of less than 200° C. At present, it is preferred to use nitromethane as the highly volatile organic solvent.

In addition to use of the volatile solvent, an organic liquid plasticizer is used as a second component of the casting solution. The CA/CAB blend is also soluble in the plasticizer. This plasticizer is characterized by having a boiling point of greater than about 200° C. and must be capable of rendering the CA and CAB compatible (i.e. leading to the formation of a homogenous CA/CAB film). Exemplary organic liquid plasticizers include the phthalates, phosphates, lactones, esters of aliphatic dibasic acids, camphor, etc. Especially preferred are the lactones including γ-butyrolactone and valerolactone. γ-Butyrolactone is presently preferred.

One of the surprising properties of butyrolactone and valerolactone is that they have high boiling points for such tiny molecules.

Although Applicants do not wish to be bound to any particular theory of operation, it is thought that the highly volatile solvent leaves the casting solution quickly while the plasticizer leaves the solution much more slowly and ultimately defines the pores in the layer as it leaves. It is preferred that the platicizer have a boiling point of about 80° F. higher than the volatile organic solvent. Since the highly volatile organic solvent will leave the solution first, the viscosity of the film increases rapidly enough so that it does not flow or sag appreciably after it is cast. The plasticizer helps to ensure that the cast film maintains its structural integrity with the pores in the film then being defined as it, the plasticizer solvent evaporates.

The first and second solvents can be used in a wide range of addition to the cellulosic esters. The volume ratio of Volatile Organic Solvent:Plasticizer may for instance vary from about 0.5–1.5 solvent:plasticizer with a ratio of about 1:1 presently preferred.

The volatile organic solvent and plasticizer must be essentially free of high molecular weight impurities, because such impurities would become concentrated as the film dries and would exert an influence on the film out of proportion to their percentage in the starting solvent.

The shape of the plasticizer molecule may also have an influence on pore geometry. Current wisdom is to the effect that linear molecules move through a film by "reptating" (i.e. a snake-like motion) which can allow the plasticizer to escape through a very irregular and tortuous pore. A substantially spherical molecule such as γ-butyrolactone, on the other hand, has a definite diameter to escape. This suggests that more spherical plasticizer molecules will produce a better-defined pore as they depart from the film.

In addition to the solvent and plasticizer, described supra., a thinner or diluent may be added, as necessary, to accurately control the viscosity of the casting solution. For example, isopropanol, methyl ethyl ketone and ethyl acetate may be mentioned as exemplary. The thinner may be added in an amount by weight of about 0.5–1.5:1 based on the weight of plasticizer added. Presently, it is preferred to use isopropanol as the thinner, present in amount of 0.88 parts by weight isopropanol: parts by weight plasticizer.

The cellulose esters are added to the highly volatile organic solvent and plasticizer in an amount sufficient to make 10–40 wt. % solutions of (cellulose esters): combined weight of cellulose esters+solvent and plasticizer).

The cellulose acetate butyrate (CAB) that is used comprises a mixture of cellulose acetic acid esters and butyric acid esters. Commercially available CABs are graded according to butyryl content of 17, 27, 38, and a 50%. Presently preferred is a CAB product having 28–31% acetyl groups and about 16% butyryl. This product is available from Eastman Kodak.

The cellulose acetate component should be of high molecular weight and good purity. Presently, this component is a film grade cellulose acetate that is commercially available from Eastman Kodak.

Figure 2:
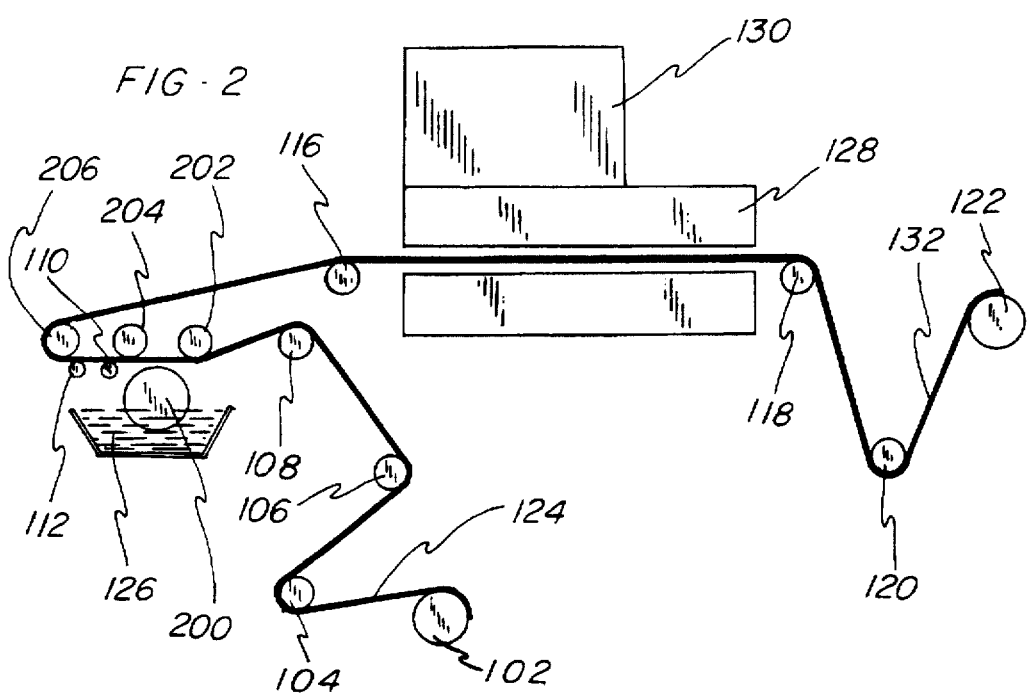
FIG. 2 is a schematic view of one coating process in accordance with the invention used to make the barrier layer of a laminated membrane such as the type shown in FIG. 1.

Turning now to FIG. 2, there is shown a Mayer Rod coating machine of the type available from Lamitec, Inc. Machines of this type are preferred for use in the instant methods for preparing the cellulose acetate/cellulose acetate butyrate films.

Feed roll 102 is provided with a wound spool of carrier film 124, preferable formed of PET. The PET is coated on the film forming side with a silicone release agent. The system is driven by take-up roll 122.

Carrier film 124 is trained around tension adjustment rolls 104, 106 and 108 and fed to and through the nip between resin transfer roller 200 and guide rollers 202, 204 and 206. In accordance with conventional techniques, the casting solution contained in bath 126 is applied to transfer roll 200 and then transferred onto the bottom surface of the carrier film. Mayer rods 110, 112 act as doctor blades and limit the coating depth to the desired thickness needed to provide a cured film of 2 microns or less. The Mayer rods 110, 112 each contain worm flights thereon with the rotating worm flights serving to spread the coating over the carrier film to the desired thickness.

In accordance with the presently preferred method, the thus coated carrier film is advanced forwardly by guide rollers 116, 118 through oven 128. In the oven, coated sheet 124 is heated to effect cure. Volatiles are vented via hood 130. Residence time of the coated carrier film 124 may vary from about 0.5 to 10 preferably around 4–5 minutes in the oven. All that is important is that the time should be sufficient to remove substantially all of the highly volatile organic solvent and plasticizer from the precursor casting solution.

The coated carrier film 124 travels through the oven at a speed of about 15 inches/minutes with the average residence time of the coating in the oven being about 4–6 minutes, preferably about 5 minutes. Hot air is circulated over the coated film from a series of five overhead air slits (not shown) formed in the top oven half with each slit having a dimension of about 11½"×⅛". The linear speed of the air emanating from each of the slits is about 1,000 linear feet/min. Each slit thereby passes about 10 cu ft/min of warm air into the oven. Accordingly, based upon the preferred residence time of about 5 minutes, each slit would pass about 50 cu. ft./min. of warm air onto the coated film. Multiplied by the number of air slits (5), during the preferred residence time, about 250 cf of warm air is circulated throughout the oven. Based upon oven residence times of 0.5–10 minutes, the coated film may be subjected to from about 25–500 cubic feet of circulating warm air.

In accordance with the preferred embodiment of the invention, it has been found critical to cure the film at a temperature of from 102° F. to 114° F., most preferably from about 106°–114° F. When cast cellulose acetate/cellulose acetate butyrate films are prepared at lower temperatures on conveyor ovens of the type shown in FIG. 2, barrier layers 32 made therefrom, when employed in polarographic glucose determination cells of the type disclosed by Newman, exhibit unacceptable "false" glucose readings due to acetaminophen presence in the analyte sample.

In the preferred method using the coating machine shown in FIG. 2 in those cases in which the casting solution is cured above the desired range, acetaminophen rejection is sufficient, but the membrane exhibits unacceptable $H_2O_2$ current sensitivity.

Although the process described above using the Mayer-rod coating machine shown in FIG. 2 is presently preferred for commercial practice, preliminary data suggest that other methods for curing the non-aqueous CA/CAB film solutions provide improvement not only in acetaminophen interference inhibition when the film is used as a barrier layer in Newman type laminated membranes, but also in hydroxyurea, potassium iodide, and isoniazid interference inhibition. Isoniazid is a commonly prescribed antibiotic that is useful in combating tuberculosis. Hydroxyurea is an antineoplastic agent that is especially useful in the treatment of carcinomas located on the head and neck regions. Potassium iodide, on the other hand, is a well-known expectorant treatment used to help relieve dyspnea. All of these compounds, when present in a diluted or undiluted blood sample can provide "false" glucose readings in polarographic instruments incorporating Newman-type glucose oxidase containing laminated membranes.

In accordance with the alternate methods, the non-aqueous CA/CAB solvent solution described above is cured at a temperature of about room temperature to about 175° C. (about 350° F.) to ultimately result in a thin film of 2 micron or less in thickness. In those instances in which room temperature curing is desired, the solvent solution must be cured for a time period of about 40 minutes or greater. Otherwise, the insufficiently cured solution, when used as a barrier layer, will not show improved interference inhibition.

As an alternative to room temperature curing, the substrate coated with solvent solution may be placed in a stationary, stagnant oven having air flow therethrough of less than about 25 cubic feet of air for a period of about 10 minutes–1 hour at a temperature of about 30° C. (86° F.) to about 175° C. (350° F.). Stagnant oven temperatures on the order of 80° C. (176° F.) to about 150° C. (302° F.) are preferred. The phrase stagnant oven means one in which the precursor CA/CAB solution is not moved or conveyed through the oven with the precursor maintained in a relatively stationary position in the oven during the curing step.

The invention will be further described with reference to the following specific examples which are to be regarded solely as being illustrative, and not as restricting the scope of the invention.

EXAMPLE 1

(a) Cellulose Acetate Butyrate In Butyrolactone Solutions 250 grams of cellulose acetate butyrate powder (Eastman Kodak) were mixed with 1000 g of butyrolactone in a 1 gallon teflon coated can. A heater blanket was placed around the can. A stir motor blade was placed into the can so that it did not touch the bottom. The can was then covered with aluminum foil and a split lid to accommodate the stirrer blade. The mixture was heated to 35° C. and stirred for four days.

(b) Cellulose Acetate In Butyrolactone

The procedure set forth in (a) above was followed except that cellulose acetate in powder form (Eastman Chemical Products) was substituted for the cellulose acetate butyrate of (a) above.

(c) 227.6 grams of cellulose acetate in butyrolactone produced in (b) above were placed in a stainless steel beaker using a large stainless steel spatula. 56.9 grams of cellulose acetate butyrate in butyrolactone produced in (a) above were added to this beaker. An additional amount of 75.0 grams of butyrolactone was added with 340.5 grams of nitromethane then added.

This resulting mixture was then stirred under a fume hood by hand until it appeared homogenous (ca. 10 minutes). 300 grams of 2-propanol were then added to the beaker while the mixture was continuously stirred.

EXAMPLE 2

Cellulose acetate/cellulose acetate butyrate solutions CA/CAB were prepared in accordance with Example 1. These solutions were each fed to the trough of a Mayer rod coating machine as shown in FIG. 1. All processing conditions utilized to produce membranes from the cellulose acetate butyrate solutions were maintained as constants except for the curing temperature in oven 128 (FIG. 2). The membrane curing temperatures are detailed in the Table. After these films had been made, they were used as a component of a laminated glucose oxidase containing membrane utilizing a polycarbonate membrane as a support layer. Glutaraldehyde was used to bind the enzyme interposed between the CA/CAB layer and the polycarbonate layer.

The CA/CAB barrier layer was less than 2 μm thick.

Glucose measurements and "false" glucose measurements due to acetaminophen presence were recorded on a YSI 2300 STATPLUS™ analyzer run in normal mode to monitor glucose levels in analyte samples using the CA/CAB containing laminated membranes. In the normal mode, current measurements are made of current running through a circuit comprising a platinum electrode and an auxiliary electrode where the potential is maintained at +0.7 v. between the electrodes. Glucose containing samples are presented to the polarographic call (and enzyme containing laminated membrane adjacent the Pt electrode) diluted at a 20:1 volume ratio of buffer solution: analyte sample. When glucose is present in the analyte sample, the instrument measures the current resulting from the amount of $H_2O_2$ present at the working anode of the polarographic test system. Polarographic cells of the type used are generally shown in the aforementioned Newman U.S. patents.

The following results were obtained under test runs designed to measure current for known samples containing 1.8 g/l glucose and those in which no glucose, but 100 mg/dl acetaminophen was present in the sample. In those instances in which no glucose, but acetaminophen, was tested, the results shown are given in terms of "apparent glucose readings". This means the current produced was compared to glucose calibration standards with the result then given in units (mg/dl) of glucose falsely detected present by the analyzer.

TABLE

| | Membrane 1 | Membrane 2 | Membrane 3 | Overall* |
|---|---|---|---|---|
| I. Membrane - CA/CAB—cured at 106° F. | | | | |
| Instrument Sensitivity for 1.8 g/l glucose nanoamps | | | | |
| (avg) | 13.76 | 12.96 | 12.7 | 13.23 |
| (std dev) | 1.07 | 0.32 | 1.1 | 0.75 |
| Apparent Glucose Reading Response To 100 mg/dl acetaminophen (given in mg/dl) | | | | |
| (avg) | 0 | 1.5 | 0 | 0.5 |
| (std dev) | 0 | 0.51 | 0 | 0.8 |
| II. Membrane - CA/CAB—cured at 100° F. | | | | |
| Instrument Sensitivity for 1.8 g/l glucose nanoamps | | | | |
| (avg) | 19.4 | 17.86 | 15.56 | 17.6 |
| (std dev) | 1.15 | 1.21 | 1.76 | 1.9 |
| Apparent Glucose Reading Response To 100 mg/dl acetaminophen (given in mg/dl) | | | | |
| (avg) | 2.79 | 2.43 | 3.11 | 2.75 |
| (std) | 0.61 | 0.04 | 0.14 | 0.28 |
| III. Membrane - CA/CAB—cured at 115° F. | | | | |
| Instrument Sensitivity for 1.8 g/l glucose nanoamps | | | | |
| (avg) | 9.17 | 7.14 | 8.77 | 8.16 |
| (std dev) | 1.34 | 0.71 | 0.61 | 0.95 |
| Apparent Glucose Reading Response To 100 mg/dl acetaminophen (given in mg/dl) | | | | |
| (avg) | 0 | 0 | 0 | 0 |
| (std dev) | 0 | 0 | 0 | 0 |

*N = 12 determinations per date point per membrane batch.

DISCUSSION—EXAMPLE 2

It is desirable that the instrument exhibit maximum current sensitivity for any given concentration of analyte. Accordingly, with only this characteristic considered, the membranes II would appear to the best since they average 17.6 nA. However, these membranes also gave the worst "false" glucose readings, averaging 2.75 mg/dl glucose readings when no glucose (but 100 mg/dl acetaminophen) was present in the sample. These "false" glucose readings are clearly unacceptable.

Batch III membranes, cured at 115° F. provided excellent "false" glucose readings at the price of unacceptably low instrument sensitivity values (i.e. average 8.16 nA).

Batch I membranes provided high sensitivity (i.e. 13.23 nA) while not providing any significant compromise in "false" glucose readings (i.e. 0.5 mg/dl).

Although Applicant is not bound to any particular theory of operation, it is thought that the Batch II membranes, cured at 100° F. resulted in relatively large pore size formation in the membrane which increased the electrical sensitivity of the membrane to glucose while also allowing easy access of acetaminophen to the working electrode. Cured at the 115° F. temperature, the Batch III membranes appeared to form tight pores that unacceptably hindered instrument sensitivity.

EXAMPLE 3

Laminated membranes containing CA/CAB barrier layers made in accordance with the procedures set forth in Examples 1 and 2 were contrasted to laminated membranes containing CA only barrier layers made in accordance with water casting methods specified in the aforementioned Newman patents. Tests were conducted to assess propensity of the membranes in falsely measuring glucose in analyte sample containing acetaminophen. In accordance with the water casting method, the cellulose acetate used for the barrier layer was deposited in a cyclohexanone/water solution.

Once again, after the requisite films had been made, they were fabricated into laminated membranes containing a polycarbonate layer as the support layer. Glucose oxidase was utilized as the enzyme and was adhered intermediate the CA or CA/CAB barrier layer and the polycarbonate support layer by the use of glutaraldehyde.

These laminated membranes were tested using a YSI Model 2300 STATPLUS™ analyzer in accordance with the procedure set forth in Example 2.

Results appear in the following Table.

| Sensitivity | Membrane # | | | |
|---|---|---|---|---|
| | 1 | 2 | 3 | *Overall |
| Batch A - CA/CAB containing laminated membrane. Tested on a model 2300 stat plus analyzer normal mode. Calibration value 1.8 g/l Glucose. N = 3 Determinations per data point per membrane. | | | | |
| nA | 14.1 | 15.1 | 12.1 | |
| | 14 | 15 | 12.7 | |
| | 14.4 | 16 | 12.5 | |
| (avg) | 14.16 | 15.36 | 12.43 | 13.98 |
| (std dev) | 0.21 | 0.55 | 0.31 | 1.31 |
| Apparent glucose response in mg/dl to 100 mg/dl acetaminophen | 0 0.01 | 0 0 | 0 0 | |
| (avg) | 0.003 | 0 | 0 | 0.001 |
| (std dev) | 0.005 | 0 | 0 | 0.0003 |
| Batch B - CA (water casting technique) containing laminated membrane. Tested on 2300 stat plus analyzer normal mode. Calibration value 1.8 g/l glucose N = 3 Determinations per data point per membrane | | | | |
| nA | 21.6 | 17.9 | | 21.72 |
| | 20.9 | 18.01 | 21.7 | |
| | 22.9 | 18.28 | 22.4 | |
| (avg) | 21.8 | 18.06 | 21.94 | 20.6 |
| (std dev) | 1.01 | 0.19 | 0.39 | 1.98 |
| Apparent glucose response in mg/dl to 100 mg/dl | 222 225 | 146 152 | 167 168 | |

| Sensitivity | Membrane # | | | |
|---|---|---|---|---|
| | 1 | 2 | 3 | *Overall |
| acetaminophen (avg) (std dev) | 226 224 2 | 155 151 4 | 167 167 0.5 | 180.88 033.4 |

*N = 9 Determinations per data point per membrane batch.

DISCUSSION—EXAMPLE 3

The laminated membrane containing a CA barrier layer produced by the water casting technique provides increased electrical sensitivity at the price of displaying high "false" glucose readings in the presence of acetaminophen.

It is apparent that the present invention provides a thin film layer suitable for use as a barrier layer in an enzyme containing laminated membrane of the type disclosed in the Newman patents. Not only do these barrier layers minimize interference that may be caused by acetaminophen presence in the analyte solution, but it achieves this goal without significantly impairing membrane sensitivity.

The CA/CAB barrier layers formed in accordance with the above when incorporated into a laminated membrane of the type shown in FIG. 1, provide an acceptable current level of from about 10 to 15 nanoamps for a 1.8 g/l analyte solution (diluted at a 20:1 buffer: analyte solution ratio) in a polarographic cell of the type wherein the electrical potential is poised at 0.7 volts. Quite surprisingly, these membranes provide improved acetaminophen rejection. That is, in polarographic cells as described above, they provide "false" glucose readings of between about only 0–2.0 mg/dl in the presence of sample solutions of 100 mg/dl acetaminophen. Most preferably, they exhibit "false" glucose readings of about 0.5 mg/dl in these systems.

The choice of volatile organic solvent and plasticizer used is not elementary. These components must:

Level promptly when spread uncommonly thin; and

Wet the web backing sufficiently to spread uniformly, without pinholes, fish eyes, orange peels or any other type of lumps or gaps in the continuity of the wet film. This is tougher than it might seem, because the web backing is chosen especially for its glossiness and slickness. Many solvents will bead up on such a web, rather than spread uniformly since we use an insoluble polyester film coated on one side with a solid silicone release layer. The fact that almost nothing sticks to the silicone allows us to peel off the cured CA/CAB film even though that film is very thin. Many commonly used solvents do not like to spread nicely on a silicone film.

EXAMPLE 4

In order to demonstrate the widespread versatility of the above disclosed alternative methods in producing barrier films that effectively inhibit acetaminophen, hydroxyurea, potassium iodide, and isoniazid interference, glucose measurement and false glucose measurements were recorded on the YSI 2300 STATPLUS™ analyzer as described in Example 2. In all cases, laminated membrane structures of the type specified in the aforementioned Newman patents were made to include thin (i.e. less than 2 micron) CA/CAB barrier films (made in accordance with the non aqueous solvent system described above in Example 1.) In each case, the enzyme used was glucose oxidase with the outer support layer composed of 5 micron thick polycarbonate having an average pore diameter of about 300 Angstrom units with a pore density of about $6 \times 10^8$ pores/cm².

PET substrates were coated with the CA/CAB non aqueous solvent system of Example 1 by using an apparatus similar to that shown in FIG. 2. Instead of passage through the oven 128 depicted in that figure, the thus coated substrates were subjected to either room temperature or stagnant oven curing under the time and temperature conditions noted in the following table.

nated membranes were also tested in conjunction with samples including the specified amounts of $H_2O_2$ (a polarographically or electrically detectable species) and with glucose containing samples. These latter mentioned tests are used to ensure that use of the CA/CAB containing barrier layers in Newman type laminated membranes resulted in acceptable electrical sensitivity levels produced at the electrode.

Results form these tests are shown in the following table:

TABLE

All Membranes were Cured external of the Lamitec machine (FIG. 2) for the temp (degrees C)/time(min) indicated in a stagnant oven

| | Average Plateau Currents (nA) | | Average Reading (g/L apparent glucose) | | | | Average | Average |
|---|---|---|---|---|---|---|---|---|
| Cure/Tem Time | H2O2 3 mg % | Glucose 1.8 g/L | Potassium Iodide 1 mM | Hydroxy- urea 1 mM | Isoniazid 1 mM | Acetaminophen 1 mM | Composite Interferen | RelComp Interference |
| RT-24HrB | | 9.069803 | 0.008093 | 0.11308 | 0.015533 | 0.007233 | 0.143939 | 0.835086 |
| RT-36Hrs | | 8.071013 | 0.001812 | 0.117244 | 0.014503 | 0.007782 | 0.14134 | 0.820011 |
| 30/10 | 7.3525 | 14.22568 | 0.001162 | 0.067824 | 0.012685 | 0.005616 | 0.087287 | 0.638023 |
| 30/30 | 5.764167 | 11.33932 | 0.000374 | 0.068306 | 0.008994 | 0.002644 | 0.080317 | 0.587077 |
| 40/10 | 6.949167 | 13.6792 | 0.00101 | 0.056803 | 0.01176 | 0.005717 | 0.075289 | 0.550324 |
| 40/30 | 7.295 | 14.31057 | 0.000968 | 0.068794 | 0.016754 | 0.008726 | 0.095242 | 0.696167 |
| 50/10 | 6.99 | 13.39114 | 0.000111 | 0.064446 | 0.011268 | 0.006522 | 0.082348 | 0.803731 |
| 50/30 | 7.681667 | 14.2703 | 0.000231 | 0.059615 | 0.010796 | 0.00533 | 0.075972 | 0.741502 |
| 60/10 | 7.635 | 14.00697 | 0.000581 | 0.054093 | 0.011969 | 0.006732 | 0.073375 | 0.71616 |
| 60/30 | 6.559167 | 11.1267 | 0.001245 | 0.058875 | 0.009543 | 0.003815 | 0.073478 | 0.717165 |
| 70/10 | 6.32 | 12.1533 | 0.001148 | 0.058768 | 0.011783 | 0.006497 | 0.078196 | 0.763208 |
| 70/30 | 7.628333 | 13.98557 | 0.000152 | 0.06366 | 0.01024 | 0.005553 | 0.079605 | 0.776964 |
| 80/10 | 6.248333 | 10.24943 | 0.001287 | 0.054268 | 0.007131 | 0.001952 | 0.064638 | 0.630877 |
| 80/30 | 6.571667 | 11.49716 | 0.000291 | 0.053736 | 0.007657 | 0.002065 | 0.063748 | 0.622197 |
| 90/10 | 5.994167 | 10.61057 | 0.000194 | 0.055517 | 0.006446 | 0.002103 | 0.064259 | 0.627178 |
| 90/30 | 6.34 | 10.80379 | 0.000212 | 0.051308 | 0.006369 | 0.002997 | 0.060887 | 0.594268 |
| 100/10 | 6.265833 | 12.07818 | 0.000332 | 0.047462 | 0.006971 | 0.002418 | 0.057182 | 0.558114 |
| 100/30 | 5.640417 | 9.96875 | 0.000332 | 0.046172 | 0.004 | 0.001039 | 0.051543 | 0.503068 |
| 115/10 | 6.2625 | 11.96989 | 0.001107 | 0.05719 | 0.010228 | 0.003778 | 0.072302 | 0.52849 |
| 115/30 | 5.734167 | 11.20432 | 0.000346 | 0.057038 | 0.00744 | 0.001876 | 0.066699 | 0.487536 |
| 130/10 | 8.085833 | 15.42966 | 0.000457 | 0.042277 | 0.004606 | 0.001511 | 0.048851 | 0.357072 |
| 130/30 | 6.8475 | 13.17761 | 0.000457 | 0.0403 | 0.0032 | 0.000403 | 0.04436 | 0.324244 |
| 150/10 | 8.753333 | 16.92 | 0.000235 | 0.027201 | 0.003794 | 0.001372 | 0.032602 | 0.238306 |
| 150/30 | 6.021667 | 11.45886 | 0 | 0.027822 | 0.002183 | 0.000504 | 0.030508 | 0.222998 |
| 175/10 | 5.084167 | 7.855795 | 5.53E-05 | 0.024222 | 0.000491 | 0.00073 | 0.025499 | 0.297913 |
| 175/30 | 5.099044 | 8.596502 | 3.55E-05 | 0.023887 | 0.0006 | 0.000572 | 0.025094 | 0.293187 |

"Average Composite Interference" is the sum of the average apparent glucose readings in g/L obtained for each of the four interferences. "Average Rel Comp Interference" is the "Average Interference Composite" obtained for any given membrane type devided by the "Average Composite Interference" obtained on the set of 106F/5 membranes (control) which were made and evaluated at the same time as the indicated experimental membranes At least four membranes of each type were evaluated.

In each case, false or apparent glucose readings were obtained for test samples containing the specified amounts of potassium iodide, hydroxyurea, isoniazid and acetaminophen acting as interferants. In this regard, a base line efficiency was established (referred to as the average relative composite interference) using CA/CAB membranes cured in accordance with the curing apparatus schematically shown in FIG. 2 and described in Example 2. Average relative composite interference values less than 1 indicate improved interference inhibition in comparison to CA/CAB barrier membranes made in accordance with Example 2 and cured at 106° F. for 5 minutes using the oven and conveyor system schematically depicted in FIG. 2. Additionally, the lami-

EXAMPLE 5

An additional series of tests were performed on the CA/CAB membranes made with the non aqueous solvent combination detailed in Example 1. Here, similar to example 4, substrates coated with the precursor solvent combination were not transported thru an oven such as that shown by reference number 128 in FIG. 2. Instead, they were subjected to room temperature (about 22° C. 72° F.) curing for the specified times. Again, similar to the other examples, the so produced CA/CAB film samples were incorporated into glucose oxidase containing Newman type laminated membranes as described above and were tested on the 2300 STATPLUS™ analyzer also described above.

Results are shown in the following table.

TABLE 3

Glucose Membrane Performance (42629) Vs. Time of CA/CAB cure at Room Temperature
Unless otherwise noted all membranes were cured external of the Lamitec machine (FIG. 2)
at room temperature for the Time (Mins.) indicated.

| | Average Plateau Currents (nA) | | Average Reading (g/L apparent glucose) | | | | Average | Average |
|---|---|---|---|---|---|---|---|---|
| Cure Time | H2O2 3 mg % | Glucose 1.8 g/L | Potassium Iodide 1 mM | Hydroxy urea 1 mM | Isoniazid 1 mM | Acetaminophen 1 mM | Composit Interferen | RelComp Interfenren |
| 106F/5° | 6.488 | 11.13 | 0.001088 | 0.091984 | 0.014988 | 0.002482 | 0.11052 | 1 |
| 0 | 0.04 | 0.1675 | 0.015583 | 0.216743 | 0.032142 | 0 | 0.264447 | 2.392759 |
| 10 | 3.398333 | 3.543333 | 0.086158 | 0.434861 | 0.182618 | 0.094742 | 0.788378 | 7.223859 |
| 20 | 2.688 | 2.1525 | 0.397588 | 1.472191 | 0.839198 | 0.4641 | 3.173077 | 28.71049 |
| 40 | 4.547143 | 5.584286 | 0.002439 | 0.146236 | 0.020846 | 0.001454 | 0.170975 | 1.54701 |
| 80 | 7.168 | 11.09 | 0.001565 | 0.071476 | 0.009035 | 0.000462 | 0.082539 | 0.746823 |
| 120 | 6.4075 | 10.23167 | 0.002169 | 0.07413 | 0.007966 | 0.006388 | 0.090632 | 0.820051 |

"Lamitec process - made and cured on machine at indicated temp (degrees F) at a web speed of 15 in/min (approx 5 min residence time)
"Average Composite Interference" is the sum of the average apparent glucose readings in g/L obtained for each of the four interferences. "Average RelComp Interference" is the "Average Interference Composite" obtained for any given membrane type devided by the "Average Composite Interference" obtained on the set of 106F/5 membranes (control) which were made and evaluated at the same time
At least four membranes of each type were evaluated

DISCUSSION EXAMPLES 4 AND 5

It is apparent that a variety of curing temperatures may be used to cure the CA/CAB film with the resulting films showing effective interference inhibition. When cured at room temperature, effective interference inhibition commences at cure times on the order of about 40 minutes and greater. In contrast, when cured in a stagnant oven, effective interference inhibition may be achieved for example after 10 or 30 minutes. In the stagnant oven, interference inhibition increases with an increase in curing temperature.

Attention is now directed to the graphical representation shown in FIG. 4. Here, the relative composite interference is shown as the y-axis with the curing temperature attained in the stagnant oven shown along the x-axis. Both 10 minute and 30 minute curing time plots are provided. Markedly increased inhibition performance is shown when curing temperatures in the oven are 80° C. (176° F.) and greater. Within this range, curing at temperatures from 80° C. (176° F.) to about 150° C. (302° F.) is particularly preferred.

FIGS. 5 and 6 demonstrate that electrical sensitivity (in terms of nanoamperes sensed at the polarographic electrode) is not significantly altered for the tests shown graphically in FIG. 4. This is important since increased interference inhibition at the expense of diminished electrical sensitivity would be of little commercial value. Importantly, in the tested 1.8 g/L glucose containing solutions, current above 10 nanoamps was detected for all curing times less than about 150° C. (302° F.). Above this temperature, electrical sensitivity begins to diminish at cure temperatures of greater than about 150° C. in the stagnant oven.

The room temperature curing tests however indicated that curing times on the order of 40 minutes and greater should be used in order to provide increased interference inhibition. This is shown graphically in FIG. 7 of the drawings wherein with cure times of less than 40 minutes curing the average relative composite interference values were greater than the baseline (i.e. greater than 1).

Figure 3:
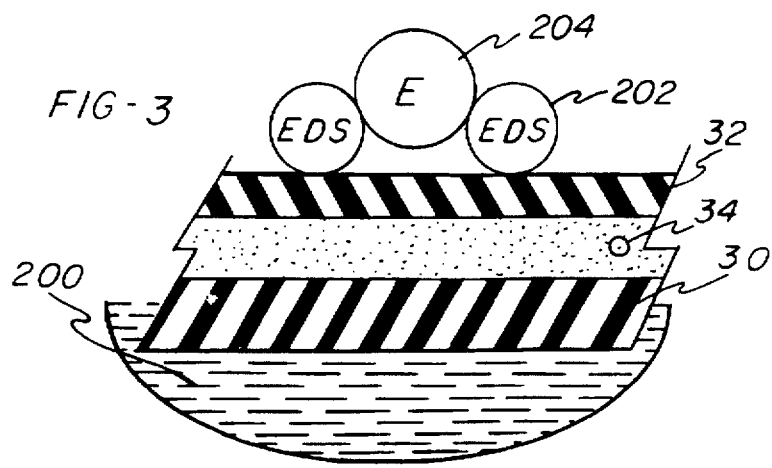
FIG. 3 is a schematic cross sectional view of a polarographic cell incorporating a laminated enzyme containing membrane having a barrier layer formed in accordance with the invention.

It is therefore apparent that the CA/CAB non aqueous solvent solutions detailed in Example 1 can be used to make a barrier film component for use in enzyme containing laminated membranes to inhibit interference or false readings caused by hydroxyurea, isoniazid, and potassium iodide. In conjunction with the schematic shown in FIG. 3, barrier layer 32 has been prepared and cured as per either the conveyor oven (FIG. 2) or stagnant oven—room temperature methods described above. When the outer support layer 30 is contacted by an aqueous sample 200 containing one or more of the interferants expressed above, the electrically detectable species 202, such as $H_2O_2$, is allowed to pass through the barrier layer 32 substantially unimpeded to provide the desired electrical measurement in conjunction with electrode 204. However, the interfering species is inhibited form such passage.

Although the current methods of producing film and films produced thereby are directed toward use of such films in enzyme containing laminate membrane structures, membranes produced in accordance with this disclosure can also be utilized in non-enzyme containing structures and methods. For example, these membranes can be used to detect and determine $H_2O_2$, hydroxylamine, hydrazine and some other important compounds which are electrochemically active without any mediating enzyme. Specificity is highly desirable in such non-enzymatic membranes, just as in an enzyme membrane, and the improved barrier films and methods of producing same disclosed herein provide significant increase in specificity without any serious loss of speed or sensitivity.

We claim:

1. In a method for preparing a thin film useful as a rejection barrier layer in an enzyme containing laminated membrane structure, the improvement comprising the steps of:

a) preparing a precursor solution comprising a cellulose ester plastic material and a solvent;

b) spreading said precursor solution over a substrate; and c) curing said precursor solution at a temperature of from about 102° F. to about 114° F. for a time sufficient to remove substantially all of said solvent from said precursor solution to form a thin film of said cellulose ester plastic material and to form a pore geometry such that said film will inhibit migration of acetaminophen therethrough while permitting passage of hydrogen peroxide.

17

2. Method as recited in claim 1 wherein said step (b) comprises spreading said solution over said substrate to a depth to form, after curing, a film of 2 microns or less in thickness.

3. Method as recited in claim 1 wherein said step (a) comprises blending cellulose acetate with cellulose acetate butyrate in a weight ratio of about 1.5–20:1 cellulose acetate to cellulose acetate butyrate.

4. Method as recited in claim 3 wherein in said step (a) said cellulose acetate is present in an amount of about 4:1 by weight based upon said cellulose acetate butyrate present.

5. Method as recited in claim 1 wherein said solvent is a highly volatile organic solvent.

6. Method as recited in claim 5 wherein said highly volatile organic solvent has a boiling point of less than 200° C.

7. Method as recited in claim 6 wherein said highly volatile organic solvent is a member of the group consisting of nitromethane, dimethylformamide, and cyclohexanone.

8. Method as recited in claim 7 wherein said highly volatile organic solvent comprises nitromethane.

9. Method as recited in claim 6 wherein said solvent also comprises a liquid organic plasticizer having a boiling point of about 200° C. or greater.

10. Method as recited in claim 9 wherein said liquid organic plasticizer is a member selected from the group consisting of phthalates, phosphates, lactones, esters of aliphatic dibasic acids, and camphor.

11. Method as recited in claim 10 wherein said liquid organic plasticizer comprises a lactone.

12. Method as recited in claim 11 wherein said lactone is butyrolactone or valerolactone.

13. Method as recited in claim 12 wherein said lactone is γ butyrolactone.

14. Method as recited in claim 1 wherein said step (c) comprises curing said solution for between about 0.5 to 10 minutes.

15. Method as recited in claim 14 wherein said curing is conducted at a temperature of about 106° F.

16. Method as recited in claim 1 further comprising adding a thinner to said solution formed in step (a).

17. Thin film made in accordance with the method of claim 1.

18. In a method of preparing a cellulosic ester film useful as a barrier layer in an enzyme containing laminated membrane structure, the improvement comprising:

forming a solution of cellulose acetate, cellulose acetate butyrate, a highly volatile organic solvent having a boiling point of less than 200° C., and a liquid organic plasticizer having a boiling point of greater than 200° C.;

coating a thin layer of said solution over a substrate;

heating said thin layer at a temperature of from about 102°–114° F. for a time sufficient to permit removal of substantially all of said volatile organic solvent and said liquid organic plasticizer from said solution and to result in a thin layer having a thickness of 2 microns or less; and subsequently separating said thin layer from said substrate.

19. Thin film made in accordance with the method of claim 18.

20. In a method of preparing a cellulosic ester film useful as an improved acetaminophen rejection barrier layer in an enzyme containing laminated membrane structure, the improvement comprising:

forming a precursor solution of cellulose acetate, cellulose acetate butyrate, a highly volatile organic solvent

18 having a boiling point of less than 200° C., and a liquid organic plasticizer having a boiling point of greater than 200° C.;

coating a thin layer of said precursor solution over a substrate;

heating said thin layer at a temperature of from about 102°–114° F. for a time sufficient to permit removal of substantially all of said volatile organic solvent and said liquid organic plasticizer from said precursor solution to form a film having a pore geometry such that said film will inhibit migration of acetaminophen therethrough while permitting passage of hydrogen peroxide and subsequently separating said film from said substrate; said coating comprising spreading said precursor solution over said substrate to a sufficient depth to provide after said heating, a film thickness of 2 microns or less.

21. Thin film made in accordance with the method of claim 20.

22. In a method of preparing a cellulose ester film useful as an improved barrier layer in an enzyme containing laminated membrane structure, the improvement comprising:

forming a precursor solution of cellulose acetate, cellulose acetate butyrate, a highly volatile organic solvent selected from the group consisting of nitromethane, dimethylformamide and cyclohexanone, and a liquid organic plasticizer chosen from the group consisting of γ-butyrolactone and valerolactone, wherein said cellulose acetate and cellulose acetate butyrate are present in an amount, by weight, of 10–40 wt. % based upon the weight of said solution;

adding a thinner to said precursor solution; then spreading a thin layer of said solution over a substrate;

curing said thin layer of precursor solution at a temperature of from 102°–114° F. for a time of about 0.5 to 1.5 minutes to form a film having a pore geometry such that said film will inhibit migration of acetaminophen therethrough while permitting passage of hydrogen peroxide; then separating said film from said substrate, said spreading comprising spreading a sufficient depth of said precursor solution over said substrate sufficient to provide after said curing, a film thickness of 2 microns or less.

23. Thin film made in accordance with the method of claim 22.

24. In a method for preparing a thin film useful as a interference rejection barrier in an enzyme containing laminated membrane the improvement comprising the steps of:

(a) preparing a precursor solution comprising a cellulose ester plastic material and a solvent;

(b) spreading said precursor solution over a substrate;

(c) curing said precursor solution at a temperature from about room temperature to about 175° C. (350° F.) for a time sufficient to remove substantially all of said solvent from said precursor solution to form a thin film of cellulose ester plastic material of about 2 microns or less in thickness and to form a pore geometry such that said film will inhibit migration of an interfering compound selected from the group consisting of acetaminophen, hydroxyurea, isoniazid, and potassium iodide therethrough while permitting passage of hydrogen peroxide therethrough.

25. Method as recited in claim 24 wherein said step (c) comprises heating said precursor solution in an oven maintained at a temperature of about 30° C. (86° F.) to about 175° C. (350° F.).

26. Method as recited in claim 25 wherein said step (c) comprises heating said precursor solution in an oven maintained at a temperature of about 80° C. (176° F.) to about 150° C. (320° F.).

27. Method as recited in claim 24 wherein said step (c) comprises curing said precursor solution at room temperature for about 40 minutes or longer.

28. Method as recited in claim 25 wherein during said step (c) said precursor solution is substantially stationary.

29. Method as recited in claim 25 wherein said step (a) comprises blending cellulose acetate with cellulose acetate butyrate in a weight ratio of about 0.5–20:1 cellulose acetate to cellulose acetate butyrate.

30. Method as recited in claim 28 wherein in said step (a) said cellulose acetate is present in an amount of about 4:1 by weight based upon said cellulose acetate butyrate present.

31. Method as recited in claim 25 wherein said solvent is a highly volatile organic solvent.

32. Method as recited in claim 31 wherein said highly volatile organic solvent has a boiling point of less than 200° C.

33. Method as recited in claim 32 wherein said highly volatile organic solvent is a member of the group consisting of nitromethane, dimethylformamide, and cyclohexanone.

34. Method as recited in claim 33 wherein said highly volatile organic solvent comprises nitromethane.

35. Method as recited in claim 32 wherein said solvent also comprises a liquid organic plasticizer having a boiling point of about 200° C. or greater.

36. Method as recited in claim 35 wherein said liquid organic plasticizer is a member selected from the group consisting of phthalates, phosphates, lactones, esters of aliphatic dibasic acids, and camphor.

37. Method as recited in claim 36 wherein said liquid organic plasticizer comprises a lactone.

38. Method as recited in claim 37 wherein said lactone is butyrolactone or valerolactone.

39. Method as recited in claim 38 wherein said lactone is γ butyrolactone.

40. Method as recited in claim 25 wherein said step (c) comprises curing said solution for between about 10 minutes to 1 hour.

41. In a polarographic measurement system of the type having an electrode, an analyte containing solution, and a laminated enzyme containing membrane interposed between said electrode and said analyte containing solution wherein said analyte containing solution contacts said enzyme and produces an electrically measurable reaction product that passes through said laminated membrane for detection at said electrode, an improved method for inhibiting interference with said detection comprising:

(a) providing an interference rejection layer of said laminated enzyme containing membrane, said interference rejection layer made by the steps of (i) preparing a precursor solution comprising a cellulose ester plastic material and a solvent;

(ii) spreading said precursor solution over a substrate; and (iii) curing said precursor solution at a temperature from about room temperature to about 175° C. (350° F.) for a time to remove substantially all of said solvent from said precursor solution to form a thin film of cellulose ester plastic material of about 2 microns or less in thickness (b) placing said interference rejection layer adjacent said electrode;

(c) providing an analyte solution comprising an analyte and an interfering compound selected from the group consisting of acetaminophen, hydroxyurea, isoniazid, and potassium iodide, (d) contacting said laminated membrane with said analyte solution, and (e) inhibiting passage of said interfering compounds through said interference rejection layer while permitting said electrically measurable species to pass through said laminated membrane for detection at said electrode.

42. Method as recited in claim 41 wherein said interfering compound comprises hydroxyurea.

43. Method as recited in claim 41 wherein said interfering compound comprises isoniazid.

44. Method as recited in claim 41 wherein said interfering compound comprises potassium iodide.

45. Method as recited in claims 42, 43, or 44 wherein said step of spreading (ii) comprises spreading a sufficient thickness of said precursor solution over said substrate to provide, after said curing, a thin film of less than 2 microns in thickness.

46. Method as recited in claim 45 wherein said curing comprises curing said precursor solution at room temperature for about 40 minutes or greater.

47. Method as recited in claim 45 wherein said curing comprises heating said precursor solution in an oven maintained at a temperature of about 30° C. (86° F.) to about 175° C. (350° F.).

48. Method as recited in claim 45 wherein said curing comprises heating said precursor solution in an oven maintained at a temperature of about 80° C. (176° F.) to about 150° C. (302° F.).

49. Method as recited in claim 48 wherein during said curing, said precursor solution is substantially stationary while in said oven.

50. Method as recited in claim 49 wherein said curing comprises heating said precursor solution for less than about 1 hour.

* * * * *